US007358402B2

(12) United States Patent
Ueda et al.

(10) Patent No.: US 7,358,402 B2
(45) Date of Patent: Apr. 15, 2008

(54) REDUCED COENZYME Q10 CRYSTAL WITH EXCELLENT STABILITY AND COMPOSITION CONTAINING SAID REDUCED COENZYME Q10 CRYSTAL

(75) Inventors: Takahiro Ueda, Hyogo (JP); Shiro Kitamura, Hyogo (JP); Taizo Kawabe, Hyogo (JP); Hideyuki Kishida, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 491 days.

(21) Appl. No.: 10/938,431

(22) Filed: Sep. 9, 2004

(65) Prior Publication Data

US 2005/0074860 A1    Apr. 7, 2005

Related U.S. Application Data

(60) Provisional application No. 60/531,524, filed on Dec. 19, 2003.

(30) Foreign Application Priority Data

Sep. 10, 2003  (JP)  ............................. 2003-318335

(51) Int. Cl.
*C07C 43/20* (2006.01)
*C07C 43/215* (2006.01)

(52) U.S. Cl. .................................................... 568/651

(58) Field of Classification Search .................... None
See application file for complete search history.

(56) References Cited

U.S. PATENT DOCUMENTS 6,184,255 B1    2/2001    Mae et al.

2004/0197418 A1    10/2004    Ueda et al.
2004/0197886 A1    10/2004    Ueda et al.
2004/0214301 A1    10/2004    Ueda et al.
2004/0215040 A1    10/2004    Ueda et al.

FOREIGN PATENT DOCUMENTS

| EP | 1 386 905 A1 | 2/2004 |
|---|---|---|
| JP | 63-188623 A | 8/1988 |
| JP | 2-212421 A | 8/1990 |
| JP | 10-109933 A | 4/1998 |
| JP | 2003-26625 A | 1/2003 |
| JP | 2003-89669 A | 3/2003 |
| JP | 2004-130201 A | 4/2004 |

(Continued)

OTHER PUBLICATIONS

Machine translation of JP2003-125734 (Cited in IDS).*

(Continued)

*Primary Examiner*—Yvonne Eyler
*Assistant Examiner*—Yevgeny Valenrod
(74) *Attorney, Agent, or Firm*—Brinks Hofer Gilson & Lione (57) ABSTRACT

The present invention provides a reduced coenzyme $Q_{10}$ crystal with excellent stability and a composition containing said reduced coenzyme $Q_{10}$ crystals.

According to the present invention, after dissolving reduced coenzyme $Q_{10}$ in a fat and oil, it is cooled, making it possible to obtain reduced coenzyme $Q_{10}$ crystals with excellent stability and which exhibit an x-ray diffraction pattern (using a CuKα emission line) that differs from ordinary reduced coenzyme $Q_{10}$ crystals. Moreover, said crystals are also excellent in bioabsorbability.

17 Claims, 2 Drawing Sheets

FOREIGN PATENT DOCUMENTS

| | | |
|---|---|---|
| WO | WO 02/090304 A1 | 11/2002 |
| WO | WO 03/006408 A1 | 1/2003 |
| WO | WO 03/006409 A1 | 1/2003 |
| WO | WO 03/006410 A1 | 1/2003 |
| WO | WO 03/006411 A1 | 1/2003 |
| WO | WO 03/006412 A1 | 1/2003 |
| WO | WO 03/008363 A1 | 1/2003 |
| WO | WO 03/032967 A1 | 4/2003 |

OTHER PUBLICATIONS

Machine translation of JP2003-089669 (Cited in IDS).*

Supplementary European Search Report from Application No. EP 04 78 7813, Nov. 23, 2006, 3 pages.

Abstract No. XP-002407208 of JP 2003-125734 A (one double sided page).

English Translation of Previously Submitted International Search Report from Corresponding International Application No. PCT/JP2004/013150, dated Dec. 14, 2004, 1 page.

Patent Cooperation Treaty International Search Report (in Japanese), From Corresponding International Application No. PCT/JP2004/013150, Dated Dec. 14, 2004, 3 pages.

* cited by examiner

REDUCED COENZYME Q10 CRYSTAL WITH EXCELLENT STABILITY AND COMPOSITION CONTAINING SAID REDUCED COENZYME Q10 CRYSTAL

RELATED APPLICATIONS

This application claims priority from Japanese Patent Application No. 2003-318335 filed Sep. 10, 2003. The application is also based on U.S. Provisional Application Ser. No. 60/531,524 filed Dec. 19, 2003.

TECHNICAL FIELD

The present invention relates to reduced coenzyme $Q_{10}$ crystals with excellent bioavailability and oxidation stability, and to a composition containing said reduced coenzyme $Q_{10}$ crystals. Reduced coenzyme $Q_{10}$ exhibits greater oral bioavailability than oxidized coenzyme $Q_{10}$, and is a compound that is useful as an ingredient in good foods, functional nutritive foods, specific health foods, nutritional supplements, nutrients, animal drugs, drinks, feeds, cosmetics, medicines, remedies, preventive drugs, etc.

BACKGROUND ART

Coenzyme Q is an essential component of organisms in wide distribution from microorganisms to mammals, and is known as a mitochondrial electron transfer system constituent in cells of living bodies. Coenzyme Q serves as a transport of the electron transfer system, operating through cycles of oxidation and reduction within the mitochondria, and reduced coenzyme Q possesses antioxidant activity. The major component of coenzyme Q in humans is coenzyme $Q_{10}$, which is a coenzyme Q species having 10 repeating structures in its side chain, and the reduced form is usually present on the order of 40 to 90% in living bodies. The physiological activity of coenzyme Q involves the activation of energy production through mitochondrial activation, activation of cardiac function, stabilization of cell membranes, cell protection through antioxidant activity, and the like.

Oxidized coenzyme $Q_{10}$ is used as a health food in the United States and Europe, and as a medication for congestive heart failure in Japan. In recent years, it has come to be used in Japan as a functional nutritive food.

On the other hand, since reduced coenzyme Q itself has strong antioxidant action, it is possible to effectively increase the antioxidant activity in blood by supplying sufficient quantities of reduced coenzyme Q to blood. Increasing the antioxidant activity in blood is thought to have a wide range of usefulness for many diseases from being aggravated supposedly by active oxygen species, for example, preventing vascular lesions during ischemia-reperfusion, preventing restenosis in arteriosclerosis, preventing vascular lesions following cerebral infarction, preventing arteriosclerosis, preventing complications of diabetes.

It is known that reduced coenzyme $Q_{10}$ can be obtained, for example, by well-known conventional processes such as synthesis, fermentation, extraction from natural sources, and the like, and then concentrating the reduced coenzyme $Q_{10}$ fraction of the effluent resulting from chromatography (Japanese Kokai Publication Hei-10-109933). In this case, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite (sodium hydrosulfite), or reduced coenzyme $Q_{10}$ to may be prepared by reacting an existing highly pure grade of coenzyme $Q_{10}$ with the reducing agent mentioned above.

Moreover, as a result of intensive research, the present inventors established processes for producing high-quality reduced coenzyme $Q_{10}$, which were disclosed in patent applications (WO 03/06408; WO 03/06409; WO 03/06410; WO 03/06411; WO 03/06412; WO 03/08363; and WO 03/32967).

However, reduced coenzyme $Q_{10}$ is readily oxidized to oxidized coenzyme $Q_{10}$ by a molecular oxygen. This oxidation is directly related to the problem of product quality such as formation of a difficult-to-remove byproduct, oxidized coenzyme $Q_{10}$, and immixture thereof into the product. In order to obtain high-purity reduced coenzyme $Q_{10}$ crystals and in order to stably maintain the obtained reduced coenzyme $Q_{10}$ crystals, it is important to suitably protect them from the above-mentioned oxidation.

SUMMARY OF THE INVENTION

Accordingly, reduced coenzyme $Q_{10}$ crystals with improved stability, and a composition containing said reduced coenzyme $Q_{10}$ crystals, as well as a process for improving the stability of reduced coenzyme $Q_{10}$ to have been desired.

As a result of intensive research carried out in view of the above-described state of affairs, the present inventors found that reduced coenzyme $Q_{10}$ crystals with excellent stability can be produced by crystallizing reduced coenzyme $Q_{10}$ in a fat and oil, and that when said crystals are analyzed by x-ray diffraction using a CuKα emission line, they possess characteristics that differ from ordinary reduced coenzyme $Q_{10}$ crystals that are crystallized from solvents, thereby achieving the present invention.

That is to say, the present invention provides a reduced coenzyme $Q_{10}$ crystal which comprises an intermediate intense peak at the diffraction angle (2θ) 3.1°, an intense peak at 20.2°, 23.0°, and a particularly intense peak at 18.7°, 19.0°, when analyzed with x-ray diffraction using a CuKα emission line.

Furthermore, the present invention provides a composition containing a reduced coenzyme $Q_{10}$ crystal wherein said reduced coenzyme $Q_{10}$ crystal coexists with a fat and oil.

Moreover, the present invention provides a preparation for oral administration which contains said reduced coenzyme $Q_{10}$ crystal or the aforementioned composition.

In addition, the present invention provides a process for producing a reduced coenzyme $Q_{10}$ crystal which comprises adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, and cooling the mixture to crystallize reduced coenzyme $Q_{10}$.

Reduced coenzyme $Q_{10}$ crystals with improved stability can be produced in accordance with the present invention.

DETAILED DESCRIPTION OF THE INVENTION

The present invention is described in detail below. In the present specification, when coenzyme $Q_{10}$ cited without specific indication, it refers to either the oxidized form or reduced form or, when both exist in admixture, a mixture of both forms.

The present invention reduced coenzyme $Q_{10}$ crystals can be produced by adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, and cooling the mixture to crystallize reduced coenzyme $Q_{10}$.

The reduced coenzyme $Q_{10}$ that is to be crystallized in the present invention can be produced by a well-known conventional process such as synthesis, fermentation, and extraction from natural sources. The reduced coenzyme $Q_{10}$ can be by itself, or can be mixed with oxidized coenzyme $Q_{10}$. Preferably, oxidized coenzyme $Q_{10}$ or a mixture of oxidized coenzyme $Q_{10}$ and reduced coenzyme $Q_{10}$, such as an existing high-purity coenzyme $Q_{10}$, can be reduced using a common reducing agent such as sodium hydrosulfite (sodium dithionite), sodium borohydride and ascorbic acid to obtain reduced coenzyme $Q_{10}$.

There are no particular limitations on the ratio of reduced coenzyme $Q_{10}$ in the total amount of coenzyme $Q_{10}$ (i.e., the total amount of reduced coenzyme $Q_{10}$ and oxidized coenzyme $Q_{10}$), but it is usually 20% by weight or more, preferably 40% by weight or more, more preferably 60% by weight or more, still more preferably 80% by weight or more, particularly preferably 90% by weight or more, and most preferably 96% by weight or more. The upper limit is 100% by weight and although there are no particular limitations, it is usually 99.9% by weight or less.

The fat and oil used can be a natural fat and oil derived from animals or plants, or a synthetic fat and oil or a processed fat and oil. Preferably, it is a species permitted for food or medicinal use. Examples of a vegetable fat and oil include coconut oil, palm oil, palm kernel oil, linseed oil, camellia oil, rice germ oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, and the like. Examples of an animal fat and oil include lard, milk fat, fish oil, beef tallow, and the like. Moreover, these can be processed to produce a fat and oil (e.g., hydrogenated oils) processed by fractionation, hydrogenation, ester exchange, or the like. Of course, medium-chain triglycerides (MCT), fatty acid partial glycerides, propylene glycol fatty acid esters, phospholipids, and the like, can be used. Mixtures of these can also be used.

Examples of medium-chain triglycerides include triglycerides of fatty acids having 6 to 12 carbons each, and preferably 8 to 12 carbons each.

Examples of fatty acid partial glycerides include monoglycerides and diglycerides of fatty acids having 6 to 18 carbons each, and preferably 6 to 12 carbons each.

Examples of propylene glycol fatty acid esters include monoglycerides and diglycerides of fatty acids having 6 to 18 carbons each, and preferably 6 to 12 carbons each.

Examples of phospholipids include egg yolk lecithin, refined soybean lecithin, phosphatidylcholine, phosphatidylethanolamine, phosphatidylserine, sphingomyelin, dicetyl phosphoric acid, stearyl amine, phosphatidylglycerol, phosphatidic acid, phosphatidyl inositolamine, cardiolipin, ceramide phosphorylethanolamine, ceramide phosphorylglycerol, and mixtures thereof.

Of the above fats and oils, vegetable fats and oils, synthetic and processed fats and oils, and phospholipids are advantageous from the standpoint of ease of handling and odor. In selecting these fats and oils, consideration should be given to price, stability of reduced coenzyme $Q_{10}$, solubility of coenzyme $Q_{10}$, and the like. For example, coconut oil, palm oil, palm kernel oil, rapeseed oil, rice oil, soybean oil, cottonseed oil, olive oil, MCT, phospholipids, and the like are advantageous, and rice oil, soybean oil, rapeseed oil, MCT, phospholipids, and the like are particularly advantageous.

A fat and oil containing reduced coenzyme $Q_{10}$ before crystallization can be obtained by heating and melting existing reduced coenzyme $Q_{10}$ crystals at the melting point of reduced coenzyme $Q_{10}$ (49° C.) or higher, and then adding to a fat and oil, or adding existing reduced coenzyme $Q_{10}$ crystals to a fat and oil, and then heating and dissolving, for example, heating to 50 to 90° C. Moreover, a solution of a fat and oil containing oxidized coenzyme $Q_{10}$ can be reduced using a reducing agent such as ascorbic acid, to produce a fat and oil containing reduced coenzyme $Q_{10}$.

There are no particular limitations on the heating/melting or heating/dissolving temperatures, but it is usually about 50° C. or higher, preferably about 55° C. or higher, more preferably about 60° C. or higher, with the upper limit usually about 90° C. or lower, preferably about 85° C. or lower, and more preferably about 80° C. or lower. It is usually carried out at about 50 to 90° C., preferably about 55 to 85° C., more preferably about 55 to 80° C., and still more preferably about 60 to 80° C.

Crystallization of reduced coenzyme $Q_{10}$ is carried out by cooling the above-mentioned fat and oil containing reduced coenzyme $Q_{10}$.

In addition to the above-mentioned fats and oils, other ingredients can be added as appropriate during the process of crystallization of reduced coenzyme $Q_{10}$. There are no particular limitations on these ingredients, and examples thereof include excipients, disintegrators, lubricants, binders, antioxidants, colorants, anticoagulation agents, absorption promoters, solubilizers for the active ingredients, stabilizers, viscosity modifier, and the like. Of course, the coexistence of active ingredients other than coenzyme $Q_{10}$ is not precluded, and the above ingredients can be added after crystallizing reduced coenzyme $Q_{10}$.

There are no particular limitations on the above-mentioned excipients, and examples thereof include white sugar, lactose, glucose, corn starch, mannitol, crystalline cellulose, calcium phosphate, calcium sulfate, and the like.

There are no particular limitations on the above-mentioned disintegrators, and examples thereof include starch, agar, calcium citrate, calcium carbonate, sodium hydrogencarbonate, dextrin, crystalline cellulose, carboxymethylcellulose, tragacanth, and the like.

There are no particular limitations on the above-mentioned lubricants, and examples thereof include talc, magnesium stearate, polyethylene glycol, silica, and the like.

There are no particular limitations on the above-mentioned binders, and examples thereof include ethyl cellulose, methyl cellulose, hydroxypropyl methylcellulose, tragacanth, shellac, gelatin, gum arabic, polyvinylpyrrolidone, polyvinylalcohol, polyacrylic acid, polymethacrylic acid, sorbitol, and the like.

There are no particular limitations on the above-mentioned antioxidants, and examples thereof include ascorbic acid, tocopherols, vitarmin A, beta-carotene, sodium hydrogensulfite, sodium thiosulfate, sodium pyrosulfite, citric acid, and the like.

There are no particular limitations on the above-mentioned colorants, and examples thereof include substances permitted for addition to pharmaceuticals and foods.

There are no particular limitations on the above-mentioned anticoagulation agents, and examples thereof include stearic acid, talc, light silicic acid anhydride, silicon dioxide hydride, and the like.

There are no particular limitations on the above-mentioned absorption promoters, and examples thereof include higher alcohols; higher fatty acids; surfactants such as sucrose fatty acid esters, sorbitan fatty acid esters, polyoxyethylene sorbitan fatty acid esters, polyglycerine fatty acid esters, and the like.

There are no particular limitations on the above-mentioned solubilizers for active ingredients, and examples thereof include fumaric acid, succinic acid, malic acid, and other organic acids, and the like.

There are no particular limitations on the above-mentioned stabilizers, and examples thereof include benzoic acid, sodium benzoate, ethyl parahydroxybenzoate, beeswax, and the like.

There are no particular limitations on the above-mentioned viscosity modifiers, and examples thereof include beeswax, and the like.

Examples of active components other than the coenzyme $Q_{10}$ include amino acids, vitamins, minerals, polyphenols, organic acids, saccharides, peptides, proteins, and the like.

There are no particular limitations on the crystallization temperature (cooling temperature during crystallization) of the reduced coenzyme $Q_{10}$, but from the standpoint of the crystallization rate, it is usually 30° C. or less, preferably 25° C. or less, more preferably 20° C. or less, still more preferably 15° C. or less, and most preferably 10° C. or less. The lower limit is the solidification temperature of the system. In ordinary practice, 0° C. to 25° C. is suitable.

The concentration of reduced coenzyme $Q_{10}$ during crystallization is the weight of reduced coenzyme $Q_{10}$ with respect to the weight of a fat and oil used, and it is preferably about 75% by weight or less, more preferably about 50% by weight or less, still more preferably about 30% by weight or less, and most preferably about 20% by weight or less. The lower limit of the concentration is usually about 0.1% by weight, preferably about 1% by weight, and more preferably about 3% by weight. Usually about 0.1 to 75% by weight, preferably about 1 to 50% by weight, and more preferably about 3 to 30% by weight is suitable for actual practice.

The thus-obtained reduced coenzyme $Q_{10}$ crystals may be used after separation, or may be used as a composition containing reduced coenzyme $Q_{10}$ crystals as being mixed with a fat and oil.

When separating reduced coenzyme $Q_{10}$ crystals after crystallization, the concentration of reduced coenzyme $Q_{10}$ during crystallization is the weight of reduced coenzyme $Q_{10}$ with respect to the weight of the fat and oil used, and it is usually about 30% by weight or less, preferably about 20% by weight or less, more preferably about 15% by weight or less, particularly preferably about 12% by weight or less, and most preferably about 10% by weight or less. By maintaining this concentration, it becomes possible to carry out crystallization and separation of the crystals on an industrial scale. From the standpoint of productivity, the lower limit of the concentration is usually about 1% by weight, and preferably about 2% by weight. Usually, crystallization and separation can be preferably carried out at about 1 to 30% by weight.

When carrying out crystallization, it is advantageous to add seed crystals so as to prevent a formation of supersaturation, and to smoothly implement nucleation and crystal growth.

Moreover, it is also possible to carry out crystallization under forced flowing. For preventing the state of supersaturation from occurring and thereby allowing nucleation and crystal growth to proceed smoothly and from the viewpoint of obtaining high-quality products, the flowing is generally brought about by a power required for stirring per unit volume of not weaker than about 0.01 kW/m$^3$, preferably not weaker than about 0.1 kW/m$^3$, and more preferably not weaker than about 0.3 kW/m$^3$. The forced flowing is generally provided by the turning of a stirring blade(s). However, the use of a stirring blade(s) is not always necessary if the above flowing can be otherwise obtained. For example, it is possible to utilize a method based on liquid circulation, and the like method.

In the process of crystallization, it is advantageous to control the crystallization weight per unit time and to control the formation of supersaturation. An advantageous crystallization weight per unit time is, for example, below a crystallization rate of about 50% of the total weight per unit time (i.e., maximum of 50% by weight/hour), and preferably below a crystallization rate of about 25% of the total crystal weight per unit time (i.e., maximum of 25% by weight/hour).

The cooling rate is usually about 40° C./hour or less, and preferably about 20° C./hour or less.

It is also allowable to separate and obtain reduced coenzyme $Q_{10}$ crystals after carrying out crystallization as above where necessary. In this case, for example, after crystallization, reduced coenzyme $Q_{10}$ crystals can be obtained as a wet product, by such a solid-liquid separation technique as centrifugation, pressure filtration, or vacuum filtration, if necessary followed by cake washing. Furthermore, they can be obtained also as a dry product by charging the wet product in a reduced pressure drier (vacuum drier) internally purged with an inert gas and drying the same under reduced pressure.

The present invention reduced coenzyme $Q_{10}$ crystals obtained as above showed different characteristics from the ordinary reduced coenzyme $Q_{10}$ crystals crystallized from solvents, when analyzed by x-ray diffraction using CuKα emission line. And these crystals exhibited outstanding stability, further showed excellent bioabsorbability.

When the reduced coenzyme $Q_{10}$ crystals of the present invention are analyzed by x-ray diffraction using a CuKα emission line, they comprise an intermediate intense peak at the diffraction angle (2θ) 3.1°, an intense peak at 20.2°, 23.0°, and a particularly intense peak at 18.7° and 19.0°, and they are distinguished from the ordinary coenzyme $Q_{10}$ crystals that are crystallized from solvents.

Preferably, the reduced coenzyme $Q_{10}$ crystals possess at least one of the following characteristics:

(a) If 100 is the peak intensity at 19.0°, the peak intensity at 3.1° is 25 or lower, and preferably 20 or lower.

(b) If 100 is the peak intensity at 19.0°, the peak intensity at 18.7° is 80 or higher, and preferably 85 or higher.

(c) The intensity ratio of the peak at 20.2° and the peak at 23.0° is peak intensity at 20.0°/peak intensity at 23.0°, namely 0.7 or higher, and preferably 0.75 or higher. More preferably, the crystals possess a combination of any two of the above characteristics (a) to (c). Even more preferably, the crystals possess a combination of all three of the above characteristics (a) to (c).

It should be noted that in indicating diffraction angles, errors could occur depending on the apparatus used, so an error on the order of ±0.2° is within the scope of the present invention.

Furthermore, in cases where the base line of the x-ray diffraction pattern is disturbed by the influence of amorphous residue in the crystals, and the like, it is advantageous to correct the base line by eliminating the interference of the amorphous matter.

After crystallizing reduced coenzyme $Q_{10}$, it can be used without further treatment as a composition wherein reduced coenzyme $Q_{10}$ crystals and a fat and oil are found together, or the coenzyme $Q_{10}$ crystals can be separated, and then used. The separated coenzyme $Q_{10}$ crystals can then be added to the desired fat and oil mentioned above, and the like, to produce a composition containing reduced coenzyme $Q_{10}$ crystals. Of course, in addition to coenzyme $Q_{10}$ crystals and a fat and oil, excipients, disintegrators, lubricants, binders, antioxidants, colorants, anticoagulation agents, absorption promoters, solubilizers for the active ingredients, stabilizers, viscosity modifiers, and active ingredients other than coenzyme $Q_{10}$, which are above mentioned, are not precluded from being added to said composition.

In the composition containing reduced coenzyme $Q_{10}$ crystals according to the present invention, the weight of reduced coenzyme $Q_{10}$ with respect to the weight of the fat and oil to be used is preferably about 75% by weight or less, more preferably about 50% by weight or less, still more preferably about 30% by weight or less, and particularly preferably about 20% by weight or less. The lower limit of concentration is usually about 0.1% by weight, preferably about 1% by weight, and more preferably about 3% by weight. Usually about 0.1 to 75% by weight, preferably about 1 to 50% by weight, and more preferably about 3 to 30% by weight is suitable for actual practice.

The present invention makes it possible to produce reduced coenzyme $Q_{10}$ crystals with excellent stability or a composition containing said reduced coenzyme $Q_{10}$ crystals. The thus-obtained crystals or composition containing said crystals are also excellent in bioabsorbability.

The resulting reduced coenzyme $Q_{10}$ crystals or composition containing said reduced coenzyme $Q_{10}$ crystals can be used as such, or can be further processed to produce capsules (hard capsules, soft capsules, or microcapsules), tablets, syrups, beverages, or other preparations for oral administration; or can be further processed to produce creams, suppositories, dentifrices, or other formulations. Preparations for oral administration are preferable, capsules are typically preferable, and soft capsules are particularly advantageous.

Of course, it is also within the scope of the present invention to form capsules containing said reduced coenzyme $Q_{10}$ crystals wherein a dissolved reduced coenzyme $Q_{10}$ in a fat and oil is formed into capsules and then cooled to be crystallized out as reduced coenzyme $Q_{10}$ crystals, said dissolved reduced coenzyme $Q_{10}$ in a fat and oil being a mixture of reduced coenzyme $Q_{10}$ and a fat and oil which is produced by adding reduced coenzyme $Q_{10}$ to a fat and oil and then heating to dissolve the reduced coenzyme $Q_{10}$ and/or by adding heat-melted reduced coenzyme $Q_{10}$ to a heated fat and oil.

There are no particular limitations on the capsule base material used for preparing capsules, and examples thereof include gelatin derived from cow bones, cowhide, pig skin, fish skin, and the like, but other base materials (substances which can be used as food additives, for example, thickeners and stabilizers derived from seaweed such as carrageenan and alginic acid, derived from plant seeds such as locust bean gum and guar gum; manufacturing agents containing celluloses, and the like) can also be used.

Furthermore, the present invention reduced coenzyme $Q_{10}$ crystals or compositions containing said reduced coenzyme $Q_{10}$ crystals, as well as the above-mentioned capsules, can be used, when appropriate, as an additive in the preparation of bread, pasta, Japanese zosui (porridge of rice and vegetables), boiled rice dishes, cakes, confectioneries, and the like. Of course, use in the preparation of other foods is not precluded.

The protection effect from oxidation of the present invention reduced coenzyme $Q_{10}$ crystals or compositions containing said reduced coenzyme $Q_{10}$ crystals can be enhanced by the manufacture and storage thereof in a deoxygenated atmosphere. A deoxygenated atmosphere can be achieved by replacement with an inert gas, pressure reduction, boiling, or combinations of these. At least, replacement with an inert gas, that is, the use of an inert gas environment, is suitable. Examples of said inert gas include nitrogen gas, helium gas, argon gas, hydrogen gas, carbonic dioxide, or the like, and nitrogen gas is preferable.

In said reduced coenzyme $Q_{10}$ crystals and compositions and preparations for oral administration containing said reduced coenzyme $Q_{10}$ crystals, it can be expected that after storage for a specified period of time, the reduced coenzyme $Q_{10}$ would be maintained in a weight ratio [reduced coenzyme $Q_{10}$/(reduced coenzyme $Q_{10}$+oxidized coenzyme $Q_{10}$)] of 90% by weight or more, and preferably 95% by weight or more. Said period of storage is, for example, 1 day or longer, preferably 1 week or longer, more preferably 1 month or longer, still more preferably a half year or longer, particularly preferably 1 year or longer, and most preferably 2 years or longer.

In accordance with the present invention, it is possible to easily produce reduced coenzyme $Q_{10}$ crystals with excellent stability or a composition containing said reduced coenzyme $Q_{10}$ crystals. Moreover, said reduced coenzyme $Q_{10}$ crystals and composition containing said crystals are excellent in bioabsorbability, and applied in wide range of fields since they are suited for such use as compositions for foods and medical use or preparations for oral administration, thus has great advantage.

BEST MODE FOR CARRYING OUT THE INVENTION

The present invention is described in further detail below with examples, but the present invention is not limited to these examples only. Furthermore, the purity of the reduced coenzyme $Q_{10}$ and the weight ratio of reduced coenzyme $Q_{10}$/oxidized coenzyme $Q_{10}$ in the examples are determined by HPLC analysis as below, but a standard for the purity of the resulting reduced coenzyme $Q_{10}$ is not established on the basis of the limiting values for purity in the present invention, and likewise, the weight ratios of reduced coenzyme $Q_{10}$/oxidized coenzyme $Q_{10}$ are not an upper limit for establishing a standard.

| (Conditions for HPLC Analysis) | |
| --- | --- |
| Column: | SYMMETRY C18 (Waters product), 250 mm (length), 4.6 mm (inner diameter) |
| Mobile phase: | Ethanol/methanol = 4/3(v/v) |
| Detection wavelength: | 210 nm |
| Flow rate: | 1 mL/min |
| Reduced coenzyme $Q_{10}$ retention time: | 9.1 min |
| Oxidized coenzyme $Q_{10}$ retention time: | 13.3 min |

In addition, an x-ray diffraction method using CuKα-emission line in Examples was carried out as follows.

| Apparatus: | rotational anticathode type x-ray diffraction apparatus Geiger-Flex RAD-rA [Rigaku Corporation product] |
| --- | --- |
| X-ray: | CuKα emission line |
| X-ray intensity: | 40 kV, 100 mA |
| Angle area: | 2θ = 2 to 60° |
| Scanning rate: | 2°/min. |
| Sampling interval: | 0.02 seconds |
| Divergence slit: | 1° |
| Receiving slit: | 0.60° |
| Scatter slit: | 1° |

REFERENCE EXAMPLE 1

To 1,000 g of ethanol was added 100 g of oxidized coenzyme $Q_{10}$ and 60 g of L-ascorbic acid. These were stirred at 78° C., and a reduction reaction was carried out. After 30 hours, it was cooled to 50° C., and 400 g of ethanol and 100 g of water were added, while maintaining the same temperature. While stirring this ethanol solution (power required for stirring per unit volume: 0.3 kW/m$^3$), it was cooled to 2° C. at a cooling rate of 10° C./hour, resulting in a white slurry. The resulting slurry was then vacuum filtered, and the wet crystals were washed successively with cold ethanol, cold water, and cold ethanol, and moreover, the wet crystals were vacuum dried (20 to 35° C., 1 to 30 mmHg) to produce 95 g of dry white crystals (yield as appearance 95 mol %). With the exception of vacuum drying, all operations were carried out in a nitrogen atmosphere. The weight ratio of reduced coenzyme $Q_{10}$/oxidized coenzyme $Q_{10}$ in the resulting crystals was 99.5/0.5.

EXAMPLE 1

Figure 1:
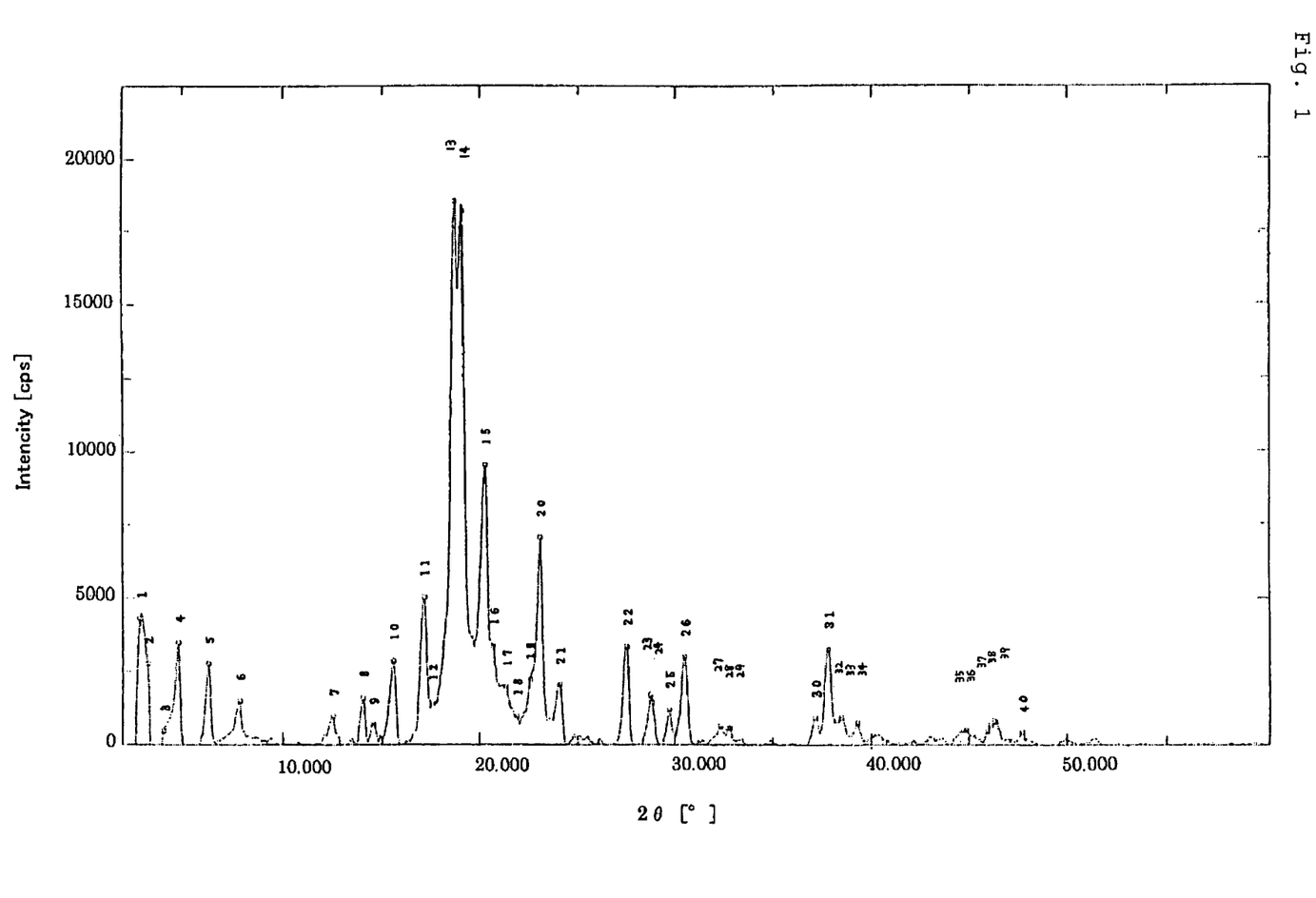
FIG. 1 is an x-ray diffraction pattern (using a CuKα emission line) of reduced coenzyme $Q_{10}$ crystals obtained by dissolving reduced coenzyme $Q_{10}$ in rapeseed oil and cooling.

10 g of the reduced coenzyme $Q_{10}$ obtained in Reference Example 1 (weight ratio of reduced coenzyme $Q_{10}$/oxidized coenzyme $Q_{10}$ was 99.5/0.5) was added to 190 g of rapeseed oil at 25° C., and while stirring at 60° C. (power required for stirring per unit volume: 0.3 kW/m$^3$), the reduced coenzyme $Q_{10}$ was completely dissolved. While further stirring (power required for stirring per unit volume: 0.3 kW/m$^3$), it was cooled to 5° C. at a cooling rate of 10° C./hour, and crystals were crystallized out. All of the above operations were carried out in a nitrogen atmosphere. The resulting slurry was vacuum filtered, and thoroughly washed with hexane, after which the wet crystals were vacuum dried (20 to 35° C., 1 to 30 mmHg), resulting in 8.7 g of reduced coenzyme $Q_{10}$ crystals, as shown in the x-ray diffraction pattern of FIG. 1, in which a CuKα emission line is used. As shown in the above x-ray diffraction pattern, these crystals comprised intermediate intense peaks at the diffraction angle (2θ) 3.1°, intense peaks at 20.2°, 23.0°, and particularly intense peaks at 18.7°, 19.0°. The weight ratio of reduced coenzyme $Q_{10}$/oxidized coenzyme $Q_{10}$ in the resulting crystals was 99.3/0.7.

EXAMPLE 2

10 g of the reduced coenzyme $Q_{10}$ obtained in Reference Example 1 (weight ratio of reduced coenzyme $Q_{10}$/oxidized coenzyme $Q_{10}$ was 99.5/0.5) was added to 190 g of a medium-chain triglyceride (MCT, C8:C10=6:4), at 25° C., and while stirring at 60° C. (power required for stirring per unit volume: 0.3 kW/m$^3$), the reduced coenzyme $Q_{10}$ was completely dissolved. While further stirring (power required for stirring per unit volume: 0.3 kW/m$^3$), it was cooled to 5° C. at a cooling rate of 10° C./hour, and crystals were precipitated out. All of the above operations were carried out in a nitrogen atmosphere. The resulting slurry was vacuum filtered, and thoroughly washed with hexane, after which the wet crystals were vacuum dried (20 to 35° C., 1 to 30 mmHg), resulting in 6.5 g of reduced coenzyme $Q_{10}$ crystals. The weight ratio of reduced coenzyme $Q_{10}$/oxidized coenzyme $Q_{10}$ in the resulting crystals was 99.3/0.7.

COMPARATIVE EXAMPLE 1

Figure 2:
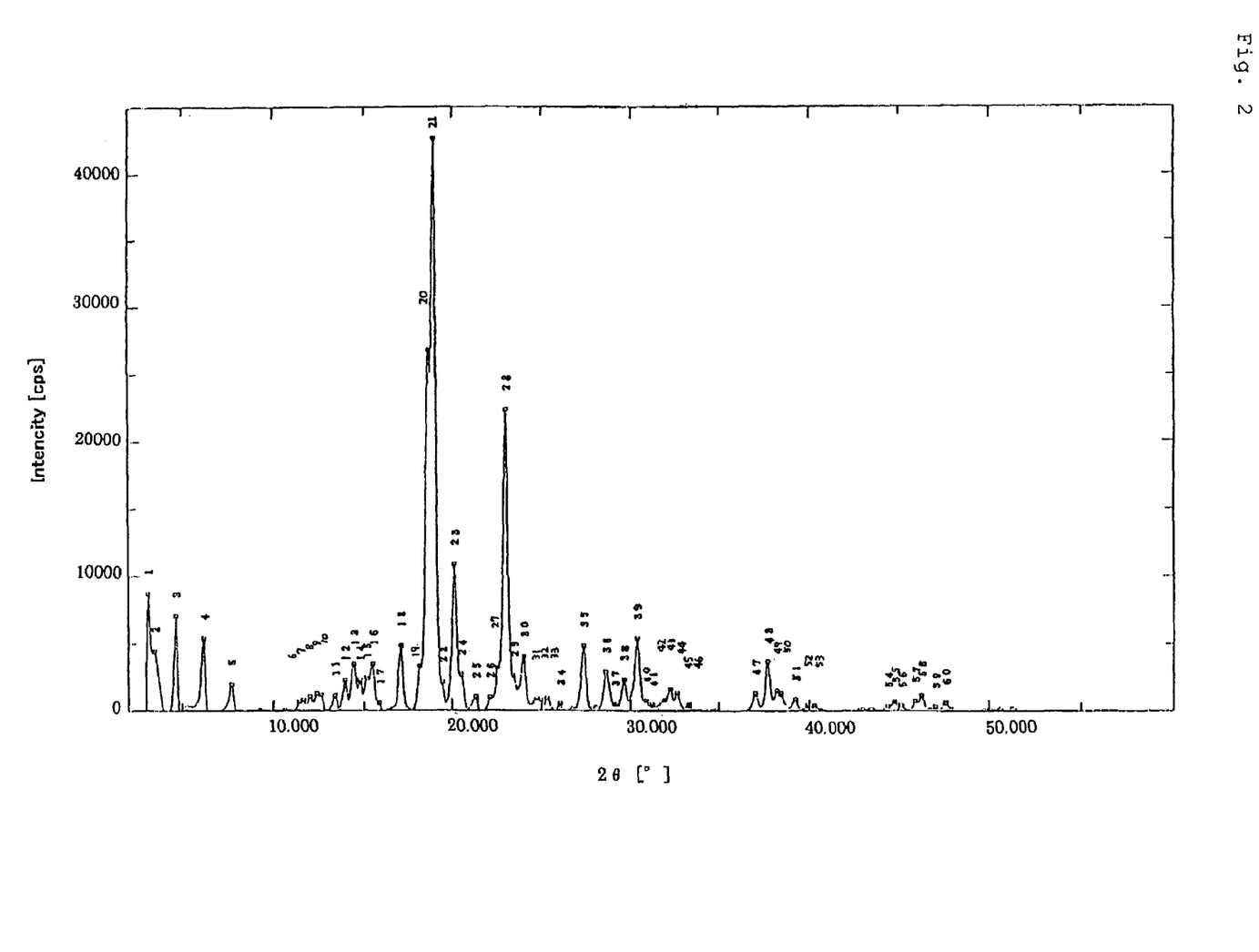
FIG. 2 is an x-ray diffraction pattern (using a CuKα emission line) of reduced coenzyme $Q_{10}$ crystals obtained by dissolving reduced coenzyme $Q_{10}$ in 6% hydrated ethanol and cooling.

10 g of the reduced coenzyme $Q_{10}$ obtained in Reference Example 1 (weight ratio of reduced coenzyme $Q_{10}$/oxidized coenzyme $Q_{10}$ was 99.5/0.5) was added to 150 g of 6% hydrated ethanol at 25° C., and while stirring at 60° C., the reduced coenzyme $Q_{10}$ was completely dissolved. While further stirring (power required for stirring per unit volume: 0.3 kW/m$^3$), it was cooled to 5° C. at a cooling rate of 10° C./hour, and crystals were precipitated out. All of the above operations were carried out in a nitrogen atmosphere. The resulting slurry was vacuum filtered, and thoroughly washed successively with ethanol, water, and ethanol, after which the wet crystals were vacuum dried (20 to 35° C., 1 to 30 mmHg), resulting in 9.6 g of reduced coenzyme $Q_{10}$ crystals, as shown in the x-ray diffraction pattern of FIG. 2, in which a CuKα emission line is used. The weight ratio of reduced coenzyme $Q_{10}$/oxidized coenzyme $Q_{10}$ in the resulting crystals was 99.3/0.7.

EXAMPLE 3

The reduced coenzyme $Q_{10}$ crystals obtained in Example 1, Example 2, and Comparative Example 1 were stored for 4 days in air at 30° C., and shielded from light. After 4 days, the weight ratio of reduced coenzyme $Q_{10}$/oxidized coenzyme $Q_{10}$ was measured. The results are given in Table 1.

TABLE 1

| | R |
| --- | --- |
| Crystals obtained in Example 1 | 96.6/3.4 |
| Crystals obtained in Example 2 | 90.5/9.5 |
| Crystals obtained in Comparative Example 1 | 79.0/21.0 |

R: Weight ratio of reduced coenzyme $Q_{10}$/oxidized coenzyme $Q_{10}$

From these results, it is found that the present invention reduced coenzyme $Q_{10}$ crystals obtained by crystallizing reduced coenzyme $Q_{10}$ from a fat and oil are excellent in stability as compared with ordinary reduced coenzyme $Q_{10}$ crystals that are crystallized from solvents.

REFERENCE EXAMPLE 2

Using the reduced coenzyme $Q_{10}$ obtained in Example 1 and the reduced coenzyme $Q_{10}$ obtained in Comparative Example 1, the blood concentrations of reduced coenzyme $Q_{10}$ were measured when they were orally administered to rats. Each samples and rapeseed oil were added to aqueous solution of 0.2% Tween 80 to prepare suspension in which reduced coenzyme $Q_{10}$:rapeseed oil=1:2. The suspension was orally administered to SD rats (male, 6 rats in one group) forcibly using a stomach sonde in 30 mg (reduced coenzyme $Q_{10}$)/kg (rat body weight). Thereafter, the blood was sampled with time, and the plasma concentration of reduced coenzyme $Q_{10}$ was measured by HPLC.

The measurement results of the plasma concentrations of reduced coenzyme $Q_{10}$ are shown in Table 2.

TABLE 2

| | $C_{max}$ (mg/ml) | $T_{max}$ (hr) | AUC (0-24) (mg/ml · hr) |
|---|---|---|---|
| Reduced coenzyme $Q_{10}$ crystals obtained in Example 1 | 1.81 ± 0.81 | 4 | 25.04 ± 6.32 |
| Reduced coenzyme $Q_{10}$ crystals obtained in Comparative Example 1 | 1.35 ± 0.27 | 8 | 21.77 ± 4.08 |
| | | | (Mean ± S.D.) |

$C_{max}$ (mg/ml) . . . Maximum plasma concentration
$T_{max}$ (hr) . . . Time to maximum plasma concentration
AUC (0-24) (mg/ml · hr) . . . Area under the plasma concentration time curve When the reduced coenzyme $Q_{10}$ crystals obtained in Example 1 and the reduced coenzyme $Q_{10}$ crystals obtained in Comparative Example 1 were administered to animals, and the plasma concentrations of coenzyme $Q_{10}$ were determined and compared, bioavailability of reduced coenzyme $Q_{10}$ of the present invention is clearly higher than those obtained by crystallization from solvents as shown in Table 2. Accordingly, it was made clear that significantly high bioavailability can be obtained when reduced coenzyme $Q_{10}$ of the present invention is used.

EXAMPLE 4

160 g of rapeseed oil, 10 g of a hydrogenated oil, 5 g of lecithin, and 5 g of beeswax were mixed at 70° C. At the same temperature, 20 g of the reduced coenzyme $Q_{10}$ obtained in Reference Example 1 (weight ratio of reduced coenzyme $Q_{10}$/oxidized coenzyme $Q_{10}$ was 99.5/0.5) was added, and while stirring (power required for stirring per unit volume: 0.3 kW/m³), the reduced coenzyme $Q_{10}$ was completely dissolved. After dissolution, the solution was cooled to 5° C. at a rate of 10° C. hour while maintaining the above stirring, and crystals were precipitated out. All of the above operations were carried out in a nitrogen atmosphere. After returning the temperature of the composition containing the reduced coenzyme $Q_{10}$ crystals to 20° C., a soft gelatin capsule preparation was produced by a conventional manner with 300 mg of the composition containing reduced coenzyme $Q_{10}$ crystals (corresponding to 30 mg of reduced coenzyme $Q_{10}$) per capsule.

EXAMPLE 5

160 g of rapeseed oil, 10 g of a hydrogenated oil, 5 g of lecithin, and 5 g of beeswax were mixed at 70° C. At the same temperature, 20 g of the reduced coenzyme $Q_{10}$ obtained in Reference Example 1 (weight ratio of reduced coenzyme $Q_{10}$/oxidized coenzyme $Q_{10}$ was 99.5/0.5) was added, and while stirring (power required for stirring per unit volume: 0.3 kW/m³), the reduced coenzyme $Q_{10}$ was completely dissolved. All of the above operations were carried out in a nitrogen atmosphere. After cooling the composition containing the reduced coenzyme $Q_{10}$ crystals to 20° C., a soft gelatin capsule preparation was produced by a conventional manner with 300 mg of the composition containing reduced coenzyme $Q_{10}$ crystals (corresponding to 30 mg of reduced coenzyme $Q_{10}$) per capsule. When this soft gelatin capsule preparation was let stand for 24 hours at 5° C., reduced coenzyme $Q_{10}$ crystals precipitated out inside the soft gel capsules.

In accordance with the present invention, it is possible to easily produce reduced coenzyme $Q_{10}$ crystals with excellent stability or a composition containing reduced coenzyme $Q_{10}$ crystals. Moreover, said reduced coenzyme $Q_{10}$ crystals and composition containing said crystals are excellent in bioabsorbability, and applied in wide range of fields since they are suited for such use as compositions for foods and medical use or preparations for oral administration, thus has great advantage.

The invention claimed is:

1. A reduced coenzyme $Q_{10}$ crystal
   which comprises an intermediate intense peak at the diffraction angle (2θ) 3.1°, an intense peak at 20.2°, 23.0°, and a particularly intense peak at 18.7°, 19.0°, when analyzed with x-ray diffraction using a CuKα emission line and
   which is obtained by adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, and cooling the mixture to separate a reduced coenzyme $Q_{10}$ crystal.

2. The reduced coenzyme $Q_{10}$ crystal according to claim 1,
   which possesses at least one of the following characteristics (a) to (c) in x-ray diffraction using a CuKα emission line:
   (a) If 100 is the peak intensity at 19.0°, the peak intensity at 3.1° is 25 or lower;
   (b) If 100 is the peak intensity at 19.0°, the peak intensity at 18.7° is 80 or higher;
   (c) The intensity ratio of the peak at 20.2° and the peak at 23.0° is peak intensity at 20.0°/peak intensity at 23.0°, namely 0.7 or higher.

3. The reduced coenzyme $Q_{10}$ crystal according to claim 2,
   wherein the weight ratio of reduced coenzyme $Q_{10}$ to the weight of a fat and oil during crystallization is 1 to 30% by weight.

4. The reduced coenzyme $Q_{10}$ crystal according to claim 2,
   wherein the fat and oil is at least one species selected from coconut oil, palm oil, palm kernel oil, linseed oil, camellia oil, rice germ oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, lard, milk fat, fish oil, beef tallow, these fats and oils processed by fractionation, hydrogenation, and/or ester exchange, medium-chain triglycerides, fatty acid partial glycerides, propylene glycol fatty acid esters, and phospholipids.

5. A composition containing a reduced coenzyme $Q_{10}$ crystal,
wherein the reduced coenzyme $Q_{10}$ crystal according to claim 1 coexists with a fat and oil.

6. The composition according to claim 5,
which is obtainable by adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, and cooling the mixture.

7. The composition according to claim 5,
which is obtainable by adding the reduced coenzyme $Q_{10}$ crystal to a fat and oil.

8. The composition according to claim 5,
wherein the weight ratio of reduced coenzyme $Q_{10}$ to the weight of a fat and oil is 0.1 to 75% by weight.

9. The composition according to claim 5,
wherein the fat and oil is at least one species selected from coconut oil, palm oil, palm kernel oil, linseed oil, camellia oil, rice germ oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, lard, milk fat, fish oil, beef tallow, these fats and oils processed by fractionation, hydrogenation and/or ester exchange, medium-chain triglycerides, fatty acid partial glycerides, propylene glycol fatty acid esters, and phospholipids.

10. A supplement for use in oral administration,
which contains the reduced coenzyme $Q_{10}$ crystal of claim 1.

11. The supplement for use in oral administration according to claim 10,
which is in capsule form.

12. The supplement for use in oral administration according to claim 11,
which is obtainable by adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, forming the mixture containing dissolved reduced coenzyme $Q_{10}$ into capsules, and cooling the resultant capsules to crystallize the reduced coenzyme $Q_{10}$.

13. A process for producing a reduced coenzyme $Q_{10}$ crystal
which comprises adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, and cooling the mixture to crystallize reduced coenzyme $Q_{10}$.

14. The process according to claim 13,
wherein the ratio of the weight of reduced coenzyme $Q_{10}$ to the weight of a fat and oil during crystallization is 0.1 to 75% by weight.

15. The process according to claim 13,
wherein the fat and oil is at least one species selected from coconut oil, palm oil, palm kernel oil, linseed oil, camellia oil, rice germ oil, rapeseed oil, rice oil, peanut oil, corn oil, wheat germ oil, soybean oil, perilla oil, cottonseed oil, sunflower seed oil, kapok oil,
evening primrose oil, shea butter, sal fat, cacao butter, sesame oil, safflower oil, olive oil, lard, milk fat, fish oil, beef tallow, these fats and oils processed by eractionation, hydrogenation and/or ester exchange, medium-chain triglycerides, fatty acid partial glycerides, propylene glycol fatty acid esters, and phospholipids.

16. The process according to claim 13,
wherein the reduced coenzyme $Q_{10}$ crystal is produced in a deoxygenated atmosphere.

17. A supplement for use in oral administration,
which is in capsule form and
contains a reduced coenzyme $Q_{10}$ crystal obtainable by adding reduced coenzyme $Q_{10}$ to a fat and oil and then heating to dissolve the reduced coenzyme $Q_{10}$ and/or adding heat-melted reduced coenzyme $Q_{10}$ to a heated fat and oil to prepare a mixture of reduced coenzyme $Q_{10}$ and a fat and oil, forming the mixture containing dissolved reduced coenzyme $Q_{10}$ into capsules, and cooling the resultant capsules.

* * * * *

UNITED STATES PATENT AND TRADEMARK OFFICE
CERTIFICATE OF CORRECTION

| | | |
|---|---|---|
| PATENT NO. | : 7,358,402 B2 | Page 1 of 1 |
| APPLICATION NO. | : 10/938431 | |
| DATED | : April 15, 2008 | |
| INVENTOR(S) | : Takahiro Ueda et al. | |

It is certified that error appears in the above-identified patent and that said Letters Patent is hereby corrected as shown below:

In the Claims

In column 14, in claim 15, lines 9-10, after "oils processed by" delete "eractionation" and substitute --fractionation-- in its place.

Signed and Sealed this

Fourteenth Day of October, 2008

JON W. DUDAS
*Director of the United States Patent and Trademark Office*